(12) United States Patent
Nguyen et al.

(10) Patent No.: US 10,100,009 B2
(45) Date of Patent: Oct. 16, 2018

(54) PRODUCTION OF TERT-BUTYL HYDROPEROXIDE SOLUTION AND PROCESS TO FORM PRODUCTS THEREFROM

(71) Applicant: Lyondell Chemical Technology, L.P., Houston, TX (US)

(72) Inventors: Ha H. Nguyen, Houston, TX (US); Te Chang, Houston, TX (US); William H. McDowell, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/726,164

(22) Filed: Oct. 5, 2017

(65) Prior Publication Data
US 2018/0099929 A1  Apr. 12, 2018

Related U.S. Application Data

(60) Provisional application No. 62/407,047, filed on Oct. 12, 2016.

(51) Int. Cl.
*C07D 301/19* (2006.01)
*C07C 407/00* (2006.01)
(Continued)

(52) U.S. Cl.
CPC ............ *C07C 407/003* (2013.01); *B01D 3/10* (2013.01); *B01D 3/143* (2013.01); *B01J 23/28* (2013.01); *C07D 301/19* (2013.01)

(58) Field of Classification Search
CPC ...... C07C 407/003; B01D 3/143; B01D 3/10; B01J 23/28; C07D 301/19
(Continued)

(56) References Cited

U.S. PATENT DOCUMENTS 2,845,461 A    7/1958   Winkler et al.
3,351,635 A   11/1967   Kollar
(Continued)

FOREIGN PATENT DOCUMENTS

EP    0410600 A2    1/1991

OTHER PUBLICATIONS

The International Search Report and Written Opinion for PCT/US2017/055404 dated Jan. 3, 2018.

*Primary Examiner* — Taylor V Oh

(57) ABSTRACT

A process for forming a concentrated solution, including distilling in a distillation zone comprised of 10 or more theoretical distillation stages, at a pressure of no greater than 300 mm Hg and a reflux ratio (D/L) of at least 1:1, an amount of an initial solution comprised of tert-butyl hydroperoxide (TBHP) in tert-butyl alcohol (TBA) having a TBHP concentration of up to 60 wt. % and a total impurity content greater than 0.01 wt. %, for a time and under distillation conditions to form a concentrated solution comprised of TBHP in TBA; and separating an overhead distillate from the distillation zone so that the concentrated solution thereafter has a TBHP concentration greater than 60 wt. %, a TBA concentration less than 40 wt. %, a water impurity content no greater than 0.1 wt. % and a total impurity content of no greater than 1 wt. %. Related epoxidation catalyst formation and epoxidation processes are also described.

19 Claims, 2 Drawing Sheets

(51) Int. Cl.
　　*B01D 3/10*　　　(2006.01)
　　*B01D 3/14*　　　(2006.01)
　　*B01J 23/28*　　(2006.01)

(58) Field of Classification Search
　　USPC .......................................................... 549/529
　　See application file for complete search history.

(56) References Cited

U.S. PATENT DOCUMENTS

| | | |
|---|---|---|
| 3,434,975 A | 3/1969 | Sheng et al. |
| 3,478,108 A | 11/1969 | Grane |
| 3,573,226 A | 3/1971 | Sorgenti |
| 3,666,777 A * | 5/1972 | Sorgenti ............... B01J 31/0202 549/529 |
| 3,849,451 A * | 11/1974 | Stein et al. .......... C07D 301/19 549/529 |
| 3,864,216 A | 2/1975 | Worrell et al. |
| 4,128,587 A | 12/1978 | Jubin |
| 4,408,081 A | 10/1983 | Foster |
| 4,988,830 A | 1/1991 | Gelb et al. |
| 5,104,493 A * | 4/1992 | Chong .................... C07C 29/80 203/6 |
| 5,107,001 A | 4/1992 | Gelb et al. |
| 5,243,084 A | 9/1993 | Cochran et al. |

\* cited by examiner

PRODUCTION OF TERT-BUTYL HYDROPEROXIDE SOLUTION AND PROCESS TO FORM PRODUCTS THEREFROM

CROSS-REFERENCE TO RELATED APPLICATIONS

This application claims the benefit of priority to U.S. Provisional Application No. 62/407,047 filed on Oct. 12, 2016, which is incorporated herein by reference in its entirety.

STATEMENT REGARDING FEDERALLY SPONSORED RESEARCH OR DEVELOPMENT

Not applicable.

FIELD OF THE INVENTION

In general, the present disclosure relates to the field of organic chemistry. More specifically, the present disclosure relates to processes for forming solutions of tert-butyl hydroperoxide and the uses thereof to form epoxides.

BACKGROUND

This section introduces information from the art that may be related to or provide context for some aspects of the techniques described herein and/or claimed below. This information is background facilitating a better understanding of that which is disclosed herein. Such background may include a discussion of "related" art. That such art is related in no way implies that it is also "prior" art. The related art may or may not be prior art. The discussion is to be read in this light, and not as admissions of prior art.

Solutions comprising tert-butyl hydroperoxide (also referred to herein as "TBHP") in the presence of tert-butyl alcohol ("TBA") have been formed in the past and have utility in various chemical reactions, including epoxidation reactions. TBHP concentrations in such solutions in some instances have been increased to 65 wt % or higher via a vacuum distillation process that lowers the concentration of TBHP in the vapor phase of the distillation column of the reactor, in order to avoid the presence of a flammable mixture in the distillation column. Non-limiting examples of such a vacuum distillation process to achieve 65 wt % TBHP solution can be found in U.S. Pat. No. 5,104,493. But previous TBHP solution formation processes have drawbacks, including yield-lowering levels of impurities and inefficient loss of TBHP in the distillation overhead streams. When a TBHP in TBA solution with yield-lowering levels of impurities is employed in epoxidation of propylene to produce propylene oxide and TBA, the impurities result in a lower yield of propylene oxide. Complicating the situation is the fact that epoxidation reactions carried out by direct injection of solutions with TBHP in TBA concentrations of 65 wt % or higher to an epoxidation reactor are highly exothermic and present operational risks associated with runaway reactions.

BRIEF SUMMARY OF THE INVENTION

Various aspects of the present disclosure address one or more of the foregoing problems in a unique and highly facile way, to yield a highly concentrated TBHP in TBA solution with a surprisingly low level of impurities and great utility in the epoxidation of propylene to produce propylene oxide. The starting material is an initial solution comprising a relatively low concentration of TBHP in TBA with one or more impurities including light components such as water, methanol, and acetone, for example. Using a distillation procedure as described in greater detail below, the starting solution is transformed into a concentrated TBHP in TBA solution having a comparatively higher concentration of TBHP and a comparatively reduced level of impurities from that of the starting material. When used as starting material in an epoxidation reaction, the concentrated TBHP in TBA solution formed in accordance with one or more embodiments of the present disclosure enables the production of an effective epoxidation catalyst as well as production of propylene oxide in a highly efficient epoxidation process as described in FIG. 2.

Thus, in one aspect of the present disclosure, there is provided a process comprising:

distilling in a distillation zone comprised of 10 or more theoretical distillation stages, at a pressure of no greater than 300 mm Hg (0.04 MPa) and a reflux ratio (D/L) of at least 1:1, an amount of an initial solution comprised of tert-butyl hydroperoxide (TBHP) in tert-butyl alcohol (TBA), the initial solution having a TBHP concentration of up to 60 wt. % and a total impurity content greater than 0.01 wt. %, for a time and under distillation conditions so that a concentrated solution comprised of TBHP in TBA is formed; and separating an overhead distillate from the distillation zone so that the concentrated solution thereafter has a TBHP concentration greater than 60 wt. %, a TBA concentration less than 40 wt. %, a water impurity content no greater than 0.1 wt. % and a total impurity content of no greater than 1 wt. %.

In some aspects of the present disclosure, the concentrated solution in this process has a tert-butyl hydroperoxide concentration of at least 65 wt. %. The reflux ratio (D/L) employed alternatively is at least 2:1. The overhead distillate has a tert-butyl hydroperoxide concentration of no more than a limit of detection in some aspects of the present disclosure. And in some aspects of the present disclosure, the total impurity content of the initial solution is in the range of 0.4 to 1 wt. %, based on the total weight of the initial solution.

Another aspect of the present disclosure provides a process that further comprises bringing together in a reaction zone:

at least a portion of the concentrated solution formed in accord with one or more embodiments of the present disclosure, a propylene solution, the propylene solution being characterized at least by having a concentration of propylene in the range of 30 to 60 wt %, based upon the combined weight of the concentrated solution and the propylene solution, and an epoxidation catalyst, for a time and under reaction conditions so that a reaction product solution comprised of propylene oxide is formed.

In some aspects of the present disclosure, in this process a first portion of the initial solution is fed to the distillation zone and a second portion of the initial solution is controllably fed into contact with a feed of the concentrated solution at one or more points downstream from the distillation zone and upstream from the reaction zone, so that that tert-butyl hydroperoxide concentration of the portion of the concentrated solution fed into the reaction zone may be selectively varied.

Yet another aspect of the present disclosure provides a process for forming an epoxidation catalyst. This process comprises bringing together (a) at least a portion of the concentrated TBHP in TBA solution made in accord with one or more embodiments of the present disclosure with (b) molybdenum, so that a catalyst solution comprising the epoxidation catalyst is formed.

While multiple aspects of the disclosure are explicitly disclosed herein, still other aspects will become apparent to those skilled in the art from the following detailed description. As will be apparent, certain aspects, as disclosed herein, are capable of modifications in various obvious ways, all without departing from the spirit and scope of the claims as presented herein. Accordingly, the drawings and detailed description are to be regarded as illustrative in nature and not restrictive.

BRIEF DESCRIPTION OF DRAWINGS

The claimed subject matter may be understood by reference to the following description of particular aspects of the present disclosure taken in conjunction with the accompanying drawing, in which like reference numerals identify like elements, and in which:

Figure 1:
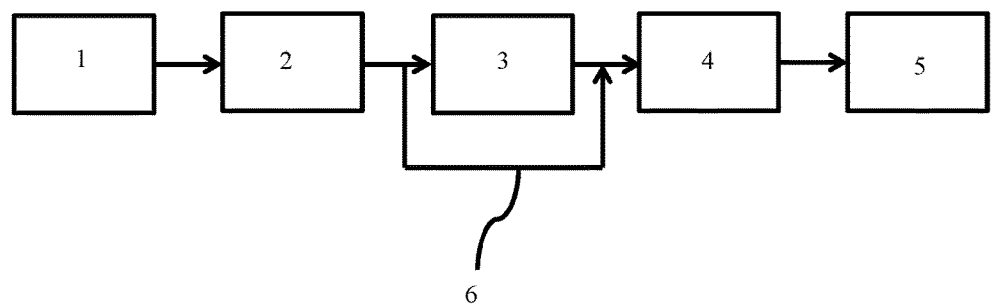
FIG. 1 illustrates a block diagram of a chemical process combining TBHP solution production, distillation and use in a catalytic epoxidation reaction, to form a reaction product comprising polypropylene oxide in accordance with one aspect of the present disclosure.
Figure 2:
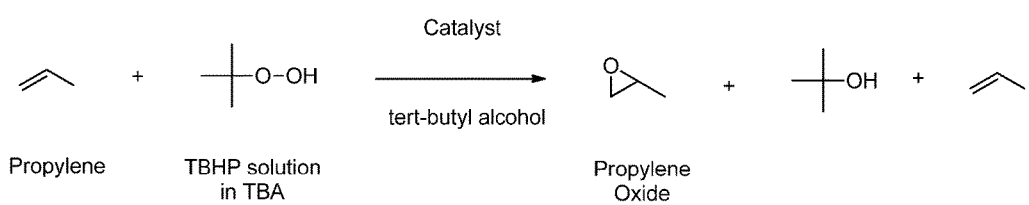
FIG. 2 illustrates an epoxidation process.

While the claimed subject matter is susceptible to various modifications and alternative forms, the drawing illustrates a specific embodiment herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope as defined by the appended claims.

DETAILED DESCRIPTION

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The embodiments illustratively disclosed herein suitably may be practiced in the absence of any element that is not specifically disclosed herein and/or any optional element disclosed herein. While compositions and methods are described in terms of "comprising," "containing," or "including" various components or steps, in at least some aspects of the present disclosure the compositions and methods can also "consist essentially of" or "consist of" the various components or steps specified. Further, while various ranges and/or numerical limitations may be expressly stated below, it should be recognized that unless expressly stated otherwise, it is intended that endpoints are to be interchangeable and any ranges include iterative ranges of like magnitude falling within the expressly stated ranges or limitations disclosed herein. It also is to be understood that each stated range sets forth every number and range encompassed within the limits of the stated range of values. It is to be noted that the terms "range" and "ranging" as used herein generally refer to a value within a specified range and encompasses all values within that entire specified range, including the end points.

As used herein, the terms "up" and "down", "upper" and "lower", "upwardly" and "downwardly", "upstream" and "downstream", "above" and "below" and other like terms indicating relative positions above or below a given point or element are used in this description to more clearly describe some aspects of the present disclosure.

Furthermore, various modifications may be made within the scope of the present disclosure as herein intended, and aspects of the present disclosure may include combinations of features other than those expressly claimed. In particular, flow arrangements other than those expressly described herein are within the scope of the present disclosure.

Various terms as used herein are shown below. To the extent a term used in a claim is not defined below, it should be given the definition persons of ordinary skill in the pertinent art have given that term as reflected in printed publications and issued patents at the time of filing. Further, unless otherwise specified, all compounds described herein may be substituted or unsubstituted and the listing of compounds includes derivatives thereof.

Processes of the present disclosure will now be described in greater detail with reference to an overall process according to one aspect of the disclosure shown in the block diagram set forth in the accompanying FIG. 1. This diagram generally illustrates a process for the production of an initial TBHP oxidate solution by, e.g., the oxidation of isobutane, formed in section (1) by a conventional manner. For example, the oxidation of isobutane may be carried out as a liquid phase oxidation using an oxygen source such as, e.g., air or molecular oxygen, brought into contact with isobutane typically at one or more temperatures in the range of about 100-200° C. and at pressures typically in the range of about 300-700 psig (2.07-4.83 MPa), optionally in the absence of metal ions or other reactants in the reaction mixture, and optionally in the presence of added water. Non-limiting examples of this and other suitable processes for producing the initial TBHP oxidate solution can be found in U.S. Pat. No. 2,845,461; U.S. Pat. No. 3,478,108; U.S. Pat. No. 5,243,084, and U.S. Pat. No. 4,408,081, the disclosures of which are incorporated by reference. This process step produces a solution having a TBHP concentration typically in a range of 30 to 48 wt % in the liquid phase. The resulting initial TBHP oxidate solution is then fed to a debutanizer (2) for the removal of isobutane in a conventional distillation manner, as both TBHP and TBA have much higher normal boiling points than that of isobutane, as described for example in U.S. Pat. No. 4,128,587 and U.S. Pat. No. 5,104,493, the disclosures of which are incorporated herein by reference. The resulting debutanized TBHP oxidate forms the initial TBHP in TBA solution which is fed as starting material to a vacuum distillation column (3) for vacuum distillation as taught in greater detail this disclosure, to form a concentrated TBHP in TBA solution. The concentrated TBHP in TBA solution is then fed to a catalytic epoxidation reactor (4) and brought into contact with an epoxidation catalyst solution under epoxidation reaction conditions as taught in this disclosure, for a time sufficient to form a product solution comprising polyethylene oxide. The resulting product solution may be fed to conventional separation and filtration equipment (5) for the recovery of various products from the product solution, typically including, e.g., propylene oxide and tert-butyl alcohol. These recovered end products have utility for the commercial production of a variety of other chemicals.

The vacuum distillation zone, in which the initial TBHP in TBA solution is concentrated to up to 60 wt %, or up to 65 wt % or higher in TBHP, may comprise at least one tray distillation column, packed column or the like. The initial TBHP in TBA solution will have a TBHP concentration of less than 60 wt %, a TBA concentration of up to 40 wt %, and a total impurity content (i.e., content of components other than TBHP and TBA) of greater than 0.1 wt %. The distillation column(s) should have at least 10 theoretical distillation stages, or alternatively at least 20 theoretical distillation stages. The reflux ratio (D/L) employed in the distillation is at least 1:1, and alternatively is at least 2:1. These distillation conditions yield a concentration of at least 60 wt %, or at least 65 wt % or greater, of TBHP in the bottom stream, with a TBA concentration of less than 40 wt. %, a water impurity content no greater than 0.1 wt. % and a total impurity content of no greater than 1 wt. %. The distillation zone may be prudently operated under an inert atmosphere to avoid formation of flammable materials in the distillation column.

Referring again to the aspect of the present disclosure illustrated in FIG. 1, a bypass line (6) and associated controlled valves are provided to control a ratio of the feed sent into the distillation zone (3) and the feed sent into the bypass line to a bottom product feed. The bypass line feed dilutes the bottom product, i.e., the concentrated TBHP in TBA solution, coming from distillation zone (3). This bypass section upstream from the epoxidation reactor (4) optionally may be equipped with an intermediate container to store an amount of the initial TBHP in TBA solution fed via the bypass line and a mixing device to mix a portion of the initial TBHP in TBA solution and the concentrated TBHP in TBA solution together prior to feeding the resulting mixture into the epoxidation reactor (4). The bypass line, control valve and optional mixing unit permit the gradual introduction of concentrated TBHP in TBA solution to the downstream epoxidation reactor, so that the concentration of TBHP in TBA solution fed from the distillation column may be modified before entering the downstream epoxidation reactor to a TBHP concentration in the range of 20-65 wt %, or alternatively 35-65 wt % or higher. Startup of the epoxidation reaction with a concentration of TBHP on the lower end of these ranges reduces the amount of heat released initially during epoxidation, avoiding formation of a temperature shock which may otherwise lead to poor performance. The typical feed of initial TBHP in TBA solution into distillation zone (3) has a TBHP concentration of about 42 wt %, but by using, e.g., a 1:1 bypass ratio, the TBHP concentration injected into the epoxidation reaction zone (4) is controlled at around 53.5 wt %, in such instance. Other feed ratios can be used depending on the concentrations of the respective TBHP in TBA solutions and the capability of the temperature control system employed in epoxidation reactor (4).

The epoxidation reactor of section (4) receives the feed of concentrated TBHP in TBA solution (alternatively diluted via bypass line (6) with an amount of the initial TBHP in TBA solution necessary to achieve the desired start up concentration of TBHP in the epoxidation reactor), for reaction with propylene and a molybdenum catalyst to form a reaction product solution comprised of propylene oxide and tert-butyl alcohol. The epoxidation reaction conditions in this zone may vary. For example, temperatures can be preferably in range from 50 to 120° C.; pressures can be from atmospheric to 1,000 psig (6.89 MPa); propylene and TBHP molar ratio can be preferably in range from 2:1 to 10:1; molybdenum catalyst concentration in epoxidation solution can be preferably in range 25 to 300 ppm. Other potential epoxidation reaction conditions may be employed. Non-limiting examples of suitable epoxidation reaction conditions may be found in U.S. Pat. No. 3,351,635, U.S. Pat. No. 5,107,001 and U.S. Pat. No. 4,988,830, all of which are incorporated herein by reference.

Typically, the molybdenum catalyst solution can be formed in the liquid phase from the concentrated TBHP in TBA solution formed according to one or more embodiments of the present disclosure, brought together with an amount of powdered or particulate, metallic molybdenum typically in the range of 20 to 10,000 ppm, preferably in range of 6,000 to 8,000 ppm, the resulting suspension being heated to one or more temperatures typically in the range of 25 to 100° C., preferably from 60 to 80° C. under pressure typically in the range of 0.1 to 0.13 MPa, or from 0 psig to 4 psig, preferably at 0 psig (0.1 MPa), for a time typically in the range of 0.25 to 2 hours, depending on the temperature employed, to give the molybdenum catalyst solution. The catalyst solution can be filtered or directly used in epoxidation. This and other non-limiting examples of suitable molybdenum catalyst preparation conditions using TBHP solution in TBA may be found in U.S. Pat. No. 3,666,777; U.S. Pat. No. 3,573,226 and U.S. Pat. No. 3,434,975, all of which are incorporated herein by reference.

It now should be appreciated that higher reaction rates can be achieved by using higher concentrations of TBHP, with resultant increase in heat release. Through use of the bypass line taught herein, an operator may control the concentration of TBHP injection into the epoxidation reactor and heat generated therein. The use of a smaller reactor is made possible while maintaining the overall productivity of the reaction in terms of propylene oxide production volume. The size of the reactor may vary and can be determined based on the specific productivity desired and the desirable concentration of TBHP in TBA solution fed into the epoxidation reactor. Moreover, low water concentration in the concentrated TBHP in TBA solution as fed into the epoxidation reactor leads to the reduction of sometimes undesirable ring opening products from propylene oxide, e.g., propylene glycol and the like. Even small amounts of water (e.g., 0.2 wt %) in the epoxidation reactor can increase the presence of such ring opening products in the epoxidation reaction product solution. Finally, the use of concentrated TBHP in TBA solutions of 60 wt %, or 65 wt % or higher, provides options to lower the temperatures used during epoxidation and catalyst concentration, while still maintaining production efficiency of the epoxidation process.

EXAMPLES

To facilitate a better understanding of the disclosure, the following examples of embodiments are given. In no way should the following examples be read to limit, or to define, the scope of the appended claims.

The analysis of organic components in the following examples was conducted using a commercially available gas chromatography made by Agilent®, such as Agilent® Model 5890 or 6890, or other suppliers. The gas chromatography was equipped with a capillary column such as RTX-624 or RTX-1 from Restek®, and a flame ionization detector. Other parameters such as oven temperature profile, carrier gas type, velocity and pressure are controlled to achieve data by following known art of gas chromatography.

The analysis of water in the following examples was conducted using a commercially available gas chromatography equipment made by Agilent®, such as Agilent Model 5890 or 6890, or other suppliers. The gas chromatography was equipped with a capillary column such as RTX-624 or RTX-1 from Restek®, and a thermal conductivity detector. Other parameters such as oven temperature profile, carrier gas type, velocity and pressure are controlled to achieve data by following known art of gas chromatography.

Samples for gas chromatography analysis were delivered online or offline directly to the instrument without further treatment.

The molybdenum catalyst used in the thereafter epoxidation examples were prepared using TBHP solution in TBA following the teaching in U.S. Pat. No. 3,666,777; U.S. Pat. No. 3,573,226 and U.S. Pat. No. 3,434,975 by mixing molybdenum metal with TBHP solution. This molybdenum concentration in the catalyst solution used in examples was adjusted by mixing with the recycle catalyst from POTBA epoxidation following the teaching in U.S. Pat. No. 3,573,226 and U.S. Pat. No. 3,666,777. The final catalyst solution in these examples typically contains 1.62 wt % molybdenum in TBA with less than 10 percent by weight of other impurities such as TBHP, mono propylene glycol, di propylene glycol, tri propylene glycol, and glycol ethers.

Example 1

200 g of 42 wt % TBHP in TBA solution was used as feed for a distillation in a tray distillation column having 20 trays, operated under a vacuum at 275 mmHg (0.037 MPa), and a reflux ratio (D/L) of 2:1 to achieve 63.6 wt % TBHP concentration at the bottom. The overhead temperature was at 61° C. The compositions of the feed and products are listed in Table 1 below.

TABLE 1

Compositions of the Feed, Bottom and overhead stream in distillation zone

| Components | Feed (wt %) | TBHP oxidate Bottom (wt %) | TBA overhead (wt %) |
|---|---|---|---|
| TBHP | 42.80 | 63.69 | — |
| TBA | 52.43 | 31.00 | 93.10 |
| Water | ~0.3 | <0.1 | — |
| Methanol | 0.24 | 0.02 | 0.70 |
| Acetone | 1.29 | 0.05 | 3.26 |

Example 1 illustrates that the high concentrated TBHP at bottom of the distillation zone has less than 0.1 wt % water, 0.02 wt % methanol and 0.05 wt % acetone.

Example 2

A propylene oxide/tert-butyl alcohol ("POTBA") epoxidation run used 246.8 g of propylene to mix with 189.8 g of 42 wt % TBHP oxidate and 5.256 g catalyst solution containing 1.62 wt % molybdenum in TBA. This mixture temperature was maintained at 117° C. using a conventional source of heating and the pressure was kept at 700-750 psig (4.83-5.17 MPa). After 65 minutes the reactor contained: 1.23 gr of TBHP and 46.8 g of PO. The TBHP conversion was 98.4%.

Example 3

A POTBA epoxidation run used 245.6 g of propylene to mix with 189.77 g of 42 wt % TBHP oxidate and 5.266 g catalyst solution containing 1.62 wt % molybdenum in TBA. This mixture was maintained at 117° C. using a conventional source of heating and the pressure was kept at 700-750 psig (4.83-5.17 MPa). After 66 minutes the reactor contained: 1.16 g of TBHP and 47.0 g of PO. The TBHP conversion was 98.5%.

Example 4

The effect of TBHP concentration on the reaction time was studied under the same conditions as shown in Examples 2 and 3. A POTBA epoxidation run used 244.0 g of propylene to mix with 123.92 g of 65 wt % concentrated TBHP in TBA solution and 5.361 g catalyst solution containing 1.62 wt % molybdenum and TBA and other components. The catalyst preparation using TBHP solution in TBA may be found in U.S. Pat. No. 3,666,777; U.S. Pat. No. 3,573,226 and U.S. Pat. No. 3,434,975. This mixture temperature was maintained at 117° C. using a conventional source of heating and the pressure was kept at 700-750 psig (4.83-5.17 MPa). After 40 minutes the reactor contained: 0.91 g of TBHP and 46.8 g of PO. The TBHP conversion was 98.8%. The byproduct propylene glycol was at 0.107 g.

Example 5

Similar to Example 4, this example was conducted to confirm the effect of TBHP concentration on the reaction time. A POTBA epoxidation run used 242.6 g of propylene to mix with 123.93 g of 65 wt % concentrated TBHP in TBA solution and 5.269 g catalyst solution containing 1.62 wt % molybdenum in TBA. This mixture was maintained at 117° C. using a conventional source of heating and the pressure was kept at 700-750 psig (4.83-5.17 MPa). After 40 minutes the reactor contained: 1.05 g of TBHP and 46.5 g of PO. The TBHP conversion was 98.7%. The byproducts propylene glycol was at 0.111 g.

Under the conditions using 65 wt % concentrated TBHP in TBA solution, the data from Examples 4 and 5 show that the reaction time is 38% faster in comparison to the time described in Examples 2 and 3 using 42 wt % initial TBHP in TBA solution. These data clearly show the faster reaction rate is achieved by using 65 wt % concentrated TBHP in TBA solution, therefore, higher initial heat release rate is expected, especially at start up.

The impact of water concentration on the POTBA epoxidation is apparent in Examples 6 and 7 below. By adding 0.543 g of water back into the 65 wt % concentrated TBHP in TBA solution, in Example 7, the amount of propylene glycol was 47% higher than that in Example 6.

Example 6

A POTBA epoxidation run used 140.5 g of propylene to mix with 135.75 g of 65 wt % concentrated TBHP in TBA solution and 4.18 g catalyst solution containing 1.62 wt % molybdenum in TBA. This mixture was maintained at 117° C. using a conventional source of heating and the pressure was kept at 700-750 psig (4.83-5.17 MPa). After 70 minutes, the reactor contained: 1.387 g of TBHP and 62.0 g of PO. The TBHP conversion was 98.5%. The byproducts propylene glycol was at 0.340 g.

Example 7

A POTBA epoxidation run used 142.43 g of propylene to mix with 135.75 g of 65 wt % concentrated TBHP in TBA solution, 4.18 g catalyst solution containing 1.62 wt % molybdenum in TBA. This mixture was maintained at 117° C. using a conventional source of heating and the pressure was kept at 700-750 psig (4.83-5.17 MPa). After 70 minutes the reactor contained: 2.09 g of TBHP and 52.65 g of PO. The TBHP conversion was 97.6%. The byproducts propylene glycol was at 0.642 g.

Example 8

The ability to conduct POTBA epoxidation at lower temperature while keeping the same production rate was studied by adjusting the temperature to have the similar reaction time as described in Example 2 and 3. For this, a POTBA epoxidation run used 247.5 g of propylene to mix with 123.51 g of 65 wt % concentrated TBHP in TBA solution and 3.508 g catalyst solution containing 1.62 wt % molybdenum in TBA. This mixture was maintained at 111° C. using a conventional source of heating and the pressure was kept at 700-750 psig (4.83-5.17 MPa). After 65 minutes, the reactor contained: 1.29 gr of TBHP and 45.4 g of PO. The TBHP conversion was 98.3%. The byproducts propylene glycol was at 0.069 g.

It is apparent that at the same reaction time as those in Examples 2 and 3 can be achieved by reducing the temperature in the reaction using 65 wt. % concentrated TBHP in TBA solution from 117° C. in Examples 4 and 5 to 111° C. in Example 8. At this temperature (111° C.), the amount of the main PO ring opening product, propylene glycol, was 38% lower than that in Example 5 at 117° C.

Example 9

A POTBA epoxidation run used 246.1 g of propylene to mix with 108.5 g of 65 wt % concentrated TBHP in TBA solution and 3.354 g catalyst solution containing 1.62 wt % molybdenum in TBA. This mixture was maintained at 113° C. using a conventional source of heating and the pressure was kept at 700-750 psig (4.83-5.17 MPa). After 65 minutes, the reactor contained: 0.675 g of TBHP and 40.75 g of PO. The TBHP conversion was 99.1%. The byproducts propylene glycol was at 0.088 g.

Similarly to Example 8, in Example 9, by conducting run at 113° C. but with 10% lower amount of 65 wt % concentrated TBHP in TBA solution (in comparison to that in Example 5), the reaction achieved the same conversion at the similar reaction time. The amount of propylene glycol was 21% lower than that in Example 5 at 117° C.

Example 10

A POTBA epoxidation run used 242.9 g of propylene to mix with 123.51 g of 65 wt % TBHP oxidate and 2.673 g catalyst solution containing 1.62 wt % molybdenum in TBA. This mixture was maintained at 117° C. using a conventional source of heating and the pressure was kept at 700-750 psig (4.83-5.17 MPa). After 65 minutes, the reactor contained: 1.153 g of TBHP and 45.45 g of PO. The TBHP conversion was 98.5%. The byproducts propylene glycol was at 0.109 g.

In Example 10, only 50% catalyst was used to maintain the same reaction time as in Example 5.

As will now be appreciated, the various aspects of the present disclosure may be embodied in a variety of forms. Examples of such aspects of the present disclosure thus include at least the following:

A1. A process comprising
distilling in a distillation zone comprised of 10 or more theoretical distillation stages, at a pressure of no greater than 300 mm Hg and a reflux ratio (D/L) of at least 1:1, an amount of an initial solution comprised of tertiary butyl hydroperoxide (TBHP) in tert-butyl alcohol (TBA), the initial solution having a TBHP concentration of up to 60 wt. % and a total impurity content greater than 0.01 wt. %, for a time and under distillation conditions so that a concentrated solution comprised of TBHP in TBA is formed; and
separating an overhead distillate from the distillation zone so that the concentrated solution thereafter has a TBHP concentration greater than 60 wt. %, a TBA concentration less than 40 wt. %, a water impurity content no greater than 0.1 wt. % and a total impurity content of no greater than 1 wt. %.

A2. The process according to A1, wherein the concentrated solution has a TBHP concentration which is at least 65 wt. %.

A3. The process according to A2, wherein the reflux ratio (D/L) is at least 2:1.

A4. The process according to A3, wherein the overhead distillate has a TBHP concentration of no more than a limit of detection.

A5. The process according to A4, wherein the total impurity content of the initial solution is in the range of 0.4 to 1 wt. %, based on the total weight of the initial solution.

A6. The process according to A1, wherein the concentrated solution has a TBHP concentration which is at least 65 wt. %.

A7. The process according to A1, wherein the reflux ratio (D/L) is at least 2:1.

A8. The process according to A1, wherein the overhead distillate has a TBHP concentration of no more than a limit of detection.

A9. The process according to A1, wherein the total impurity content of the initial solution is in the range of 0.4 to 1 wt. %, based on the total weight of the initial solution.

B1. A process according to any of A1-A9, further comprising bringing together in a reaction zone:
at least a portion of the concentrated solution,
a propylene solution, the propylene solution being characterized at least by having a concentration of propylene in the range of 30 to 60 wt %, based upon the combined weight of the solution of TBHP in TBA and the propylene solution, and
an epoxidation catalyst,
for a time and under reaction conditions so that a reaction product solution comprised of propylene oxide is formed.

B2. The process according to B1, wherein a first portion of the initial solution is fed to the distillation zone and a second portion of the initial solution is controllably fed into contact with a feed of the concentrated solution at one or more points downstream from the distillation zone and upstream from the reaction zone, so that that TBHP concentration of the portion of the concentrated solution fed into the reaction zone may be selectively varied.

B3. The process according to B2, wherein the epoxidation catalyst comprises molybdenum.

B4. The process according to any of B1-B2, further comprising forming an epoxidation catalyst by a process comprising bringing together at least a portion of the concentrated solution with molybdenum so that a catalyst solution comprising the epoxidation catalyst is formed.

C1. A process according to any of A1-A9, further comprising forming an epoxidation catalyst by a process comprising bringing together at least a portion of the concentrated solution with molybdenum so that a catalyst solution comprising the epoxidation catalyst is formed.

While the foregoing is directed to various specific aspects of this disclosure, other and further aspects of the disclosure may be devised without departing from the scope thereof, such scope being as determined by the claims that follow.

What is claimed is:

1. A process comprising
   distilling in a distillation zone comprised of 10 or more theoretical distillation stages, at a pressure of no greater than 0.04 MPa and a reflux ratio (D/L) of at least 1:1, an amount of an initial solution comprised of tert-butyl hydroperoxide in tert-butyl alcohol, the initial solution having a tert-butyl hydroperoxide concentration of up to 60 wt. % and a total impurity content greater than 0.01 wt. %, for a time and under distillation conditions so that a concentrated solution comprised of tert-butyl hydroperoxide in tert-butyl alcohol is formed; and
   separating an overhead distillate from the distillation zone so that the concentrated solution thereafter has a tert-butyl hydroperoxide concentration greater than 60 wt. %, a tert-butyl alcohol concentration less than 40 wt. %, a water impurity content no greater than 0.1 wt. % and a total impurity content of no greater than 1 wt. %.

2. The process according to claim 1, wherein the concentrated solution has a tert-butyl hydroperoxide concentration of at least 65 wt. %.

3. The process according to claim 2, wherein the reflux ratio (D/L) is at least 2:1.

4. The process according to claim 3, wherein the overhead distillate has a tert-butyl hydroperoxide concentration of no more than a limit of detection.

5. The process according to claim 4, wherein the total impurity content of the initial solution is in the range of 0.4 to 1 wt. %, based on the total weight of the initial solution.

6. A process according to claim 5, further comprising bringing together in a reaction zone:
   at least a portion of the concentrated solution,
   a propylene solution, the propylene solution being characterized at least by having a concentration of propylene in the range of 30 to 60 wt %, based upon the combined weight of the concentrated solution and the propylene solution, and
   an epoxidation catalyst,
   for a time and under reaction conditions so that a reaction product solution comprised of propylene oxide is formed.

7. A process according to claim 5, further comprising forming an epoxidation catalyst by a process comprising bringing together at least a portion of the concentrated solution with molybdenum so that a catalyst solution comprising the epoxidation catalyst is formed.

8. A process according to claim 3, further comprising bringing together in a reaction zone:
   at least a portion of the concentrated solution,
   a propylene solution, the propylene solution being characterized at least by having a concentration of propylene in the range of 30 to 60 wt %, based upon the combined weight of the concentrated solution and the propylene solution, and
   an epoxidation catalyst,
   for a time and under reaction conditions so that a reaction product solution comprised of propylene oxide is formed.

9. A process according to claim 3, further comprising forming an epoxidation catalyst by a process comprising bringing together at least a portion of the concentrated solution with molybdenum so that a catalyst solution comprising the epoxidation catalyst is formed.

10. The process according to claim 1, wherein the concentrated solution has a tert-butyl hydroperoxide concentration which is at least 65 wt. %.

11. The process according to claim 1, wherein the reflux ratio (D/L) is at least 2:1.

12. The process according to claim 1, wherein the overhead distillate has a tert-butyl hydroperoxide concentration of no more than a limit of detection.

13. The process according to claim 1, wherein the total impurity content of the initial solution is in the range of 0.4 to 1 wt. %, based on the total weight of the initial solution.

14. A process according to claim 1, further comprising bringing together in a reaction zone:
   at least a portion of the concentrated solution,
   a propylene solution, the propylene solution being characterized at least by having a concentration of propylene in the range of 30 to 60 wt %, based upon the combined weight of the concentrated solution and the propylene solution, and
   an epoxidation catalyst,
   for a time and under reaction conditions so that a reaction product solution comprised of propylene oxide is formed.

15. The process according to claim 14, wherein a first portion of the initial solution is fed to the distillation zone and a second portion of the initial solution is controllably fed into contact with a feed of the concentrated solution at one or more points downstream from the distillation zone and upstream from the reaction zone, so that that tert-butyl hydroperoxide concentration of the portion of the concentrated solution fed into the reaction zone may be selectively varied.

16. The process according to claim 15, wherein the epoxidation catalyst comprises molybdenum.

17. The process according to claim 16, further comprising forming an epoxidation catalyst by a process comprising bringing together at least a portion of the concentrated solution with molybdenum so that a catalyst solution comprising the epoxidation catalyst is formed.

18. The process according to claim 14, further comprising forming an epoxidation catalyst by a process comprising bringing together at least a portion of the concentrated solution with molybdenum so that a catalyst solution comprising the epoxidation catalyst is formed.

19. A process according to claim 1, further comprising forming an epoxidation catalyst by a process comprising bringing together at least a portion of the concentrated solution with molybdenum so that a catalyst solution comprising the epoxidation catalyst is formed.

* * * * *